(12) United States Patent
Chierchia et al.

(10) Patent No.: US 9,259,235 B2
(45) Date of Patent: Feb. 16, 2016

(54) ADAPTABLE DEVICE FOR ELECTRICALLY ISOLATING PULMONARY VEINS IN ATRIAL FIBRILLATION

(75) Inventors: Gian Battista Chierchia, Brussels (BE); Enrico Perfler, Lavagna (IT)

(73) Assignee: ATRICATH S.R.L., Milan (IT)

( * ) Notice: Subject to any disclaimer, the term of this patent is extended or adjusted under 35 U.S.C. 154(b) by 174 days.

(21) Appl. No.: 14/112,340

(22) PCT Filed: Apr. 12, 2012

(86) PCT No.: PCT/EP2012/056626
§ 371 (c)(1),
(2), (4) Date: Oct. 17, 2013

(87) PCT Pub. No.: WO2012/143283
PCT Pub. Date: Oct. 26, 2012

(65) Prior Publication Data
US 2014/0052062 A1   Feb. 20, 2014

(30) Foreign Application Priority Data
Apr. 18, 2011   (IT) .............................. GE2011A0043

(51) Int. Cl.
*A61B 17/3203*   (2006.01)
*A61B 18/02*   (2006.01)
(Continued)

(52) U.S. Cl.
CPC ............. *A61B 17/3203* (2013.01); *A61B 18/02* (2013.01); *A61B 18/04* (2013.01);
(Continued)

(58) Field of Classification Search
CPC .............. A61B 18/24; A61B 18/201; A61B 2018/00351; A61B 2018/00577; A61B 2018/00023; A61B 2018/1475; A61B 2018/1492; A61B 2018/00214; A61B 2018/00273; A61B 2218/002; A61B 2017/22048; A61B 2017/22054; A61B 2017/22061; A61B 2017/22062; A61B 2017/22069; A61B 2017/3486; A61B 17/3203; A61N 2005/0602
See application file for complete search history.

(56) References Cited

U.S. PATENT DOCUMENTS 3,874,388 A   4/1975   King et al.
6,652,515 B1 *  11/2003   Maguire ................ A61B 18/00
                                                    606/41
(Continued)

FOREIGN PATENT DOCUMENTS

WO   WO 2011055143 A2 *  5/2011   ............. A61B 17/22

OTHER PUBLICATIONS

International Search Report for corresponding PCT Application No. PCT/EP2012/056626, mailed May 6, 2012.

*Primary Examiner* — Gary Jackson
*Assistant Examiner* — Joshua Rosefelt
(74) *Attorney, Agent, or Firm* — Greer, Burns & Crain, Ltd.

(57) ABSTRACT

A device for electrically isolating pulmonary veins in atrial fibrillation for treatment thereof by ablation of a circumferential zone of tissue. The device includes a catheter (with terminal and distal parts) and comprising a first tubular element; a second tubular element concentric with the first tubular element and an axial rod-like element which extends beyond the distal end of the first and second tubular elements; and a first tubular toroidal element supported by tubular arms extending from the distal end towards the toroidal element, forming a cage which can be opened in umbrella fashion around the distal end of the catheter. The tubular arms and the toroidal element are in fluid communication with each other and with the tubular element of the catheter. The device also includes a second toroidal tubular element in fluid communication by means of the radial arms with the first tubular element of the catheter.

11 Claims, 4 Drawing Sheets

(51) Int. Cl.
*A61B 18/14* (2006.01)
*A61B 18/04* (2006.01)
*A61B 18/00* (2006.01)
*A61N 7/02* (2006.01)
*A61B 18/18* (2006.01)
*A61B 19/00* (2006.01)

(52) U.S. Cl.
CPC ............ *A61B18/1492* (2013.01); *A61B 18/18* (2013.01); *A61B 18/1815* (2013.01); *A61B 2018/00214* (2013.01); *A61B 2018/00375* (2013.01); *A61B 2018/0212* (2013.01); *A61B 2018/1861* (2013.01); *A61B 2019/5433* (2013.01); *A61B 2019/5466* (2013.01); *A61N 7/022* (2013.01)

(56) References Cited

U.S. PATENT DOCUMENTS

| | | |
|---|---|---|
| 2004/0243118 A1* | 12/2004 | Ayers .................. A61B 5/0422 606/21 |
| 2005/0165391 A1 | 7/2005 | Maguire et al. |
| 2005/0234436 A1 | 10/2005 | Baxter et al. |
| 2005/0234437 A1 | 10/2005 | Baxter et al. |
| 2006/0224153 A1* | 10/2006 | Fischell ............. A61B 18/1492 606/41 |
| 2006/0271032 A1 | 11/2006 | Chin et al. |
| 2007/0066878 A1 | 3/2007 | Worley et al. |
| 2007/0083195 A1 | 4/2007 | Werneth et al. |

\* cited by examiner

ADAPTABLE DEVICE FOR ELECTRICALLY ISOLATING PULMONARY VEINS IN ATRIAL FIBRILLATION

The present invention relates to a device for the treatment of atrial fibrillation by means of an ablation method performed using a catheter inserted into the orifice of pulmonary veins.

In the context of intracardial ablation applications, the term "ablation" is understood as meaning a sufficient alteration of the properties of the tissue such as to stop substantially the conduction of electrical signals from and through the ablated cardiac tissue.

The published patent application US 2005/0165391 A1 discloses an ablation device for electrically isolating the orifice of a pulmonary vein from an atrial wall by means of a catheter comprising a circumferential ablation element comprising a plurality of form-memory metallic filaments adjustable between different configurations so as to allow their introduction into the atrium and ablative engagement between the ablation elements and the circumferential tissue zone. The use of these form-memory metallic filaments, however, gives rise to numerous problems in connection with their precise adjustment in the tissue zone to be ablated, owing to the reduced flexibility of said rigid or semi-rigid structures. Moreover the presence of rigid metallic structures may easily cause damage to the tissue.

The object of the present invention is therefore to provide a device which allows the treatment of atrial fibrillation by means of an ablation method performed using a catheter inserted into the orifice of the pulmonary veins, where all the positioning and ablation operations are performed using inflatable filament-like tubes.

This object is achieved by means of a device as claimed in Claim 1.

Further objects and advantages of the device according to the present invention will emerge more clearly during the course of the following description of a preferred embodiment thereof, provided with reference to the accompanying drawings in which.

As is known, the heart has two upper cavities called "right atrium and left atrium" separated by a wall called "interatrial septum". The two venae cavae and the coronary sinus emerge inside the right atrium, while the four pulmonary veins which convey the blood oxygenated in the lungs emerge inside the left atrium.

During the normal heartbeat the impulse generated by the sinoatrial node causes contraction of the heart muscle and allows pumping of the blood. In atrial fibrillation, the electrical impulses which give rise to contraction of the atria are activated in a totally random and fragmentary manner, resulting in multiple wave fronts and disorganized and fragmentary contractions. These contractions of the atria are often inefficient from a haemodynamic point of view and therefore do not allow the heart to perform its pumping function in an efficient manner.

Many means for restoring the sinus rhythm or "cardioversion" of the heart, such as pharmacological or electrical cardioversion, have been proposed. Recently transcatheter ablation has also been introduced with success, this technique being used to interrupt the electrical transmission from the pulmonary veins to the left atrium.

Figure 1:
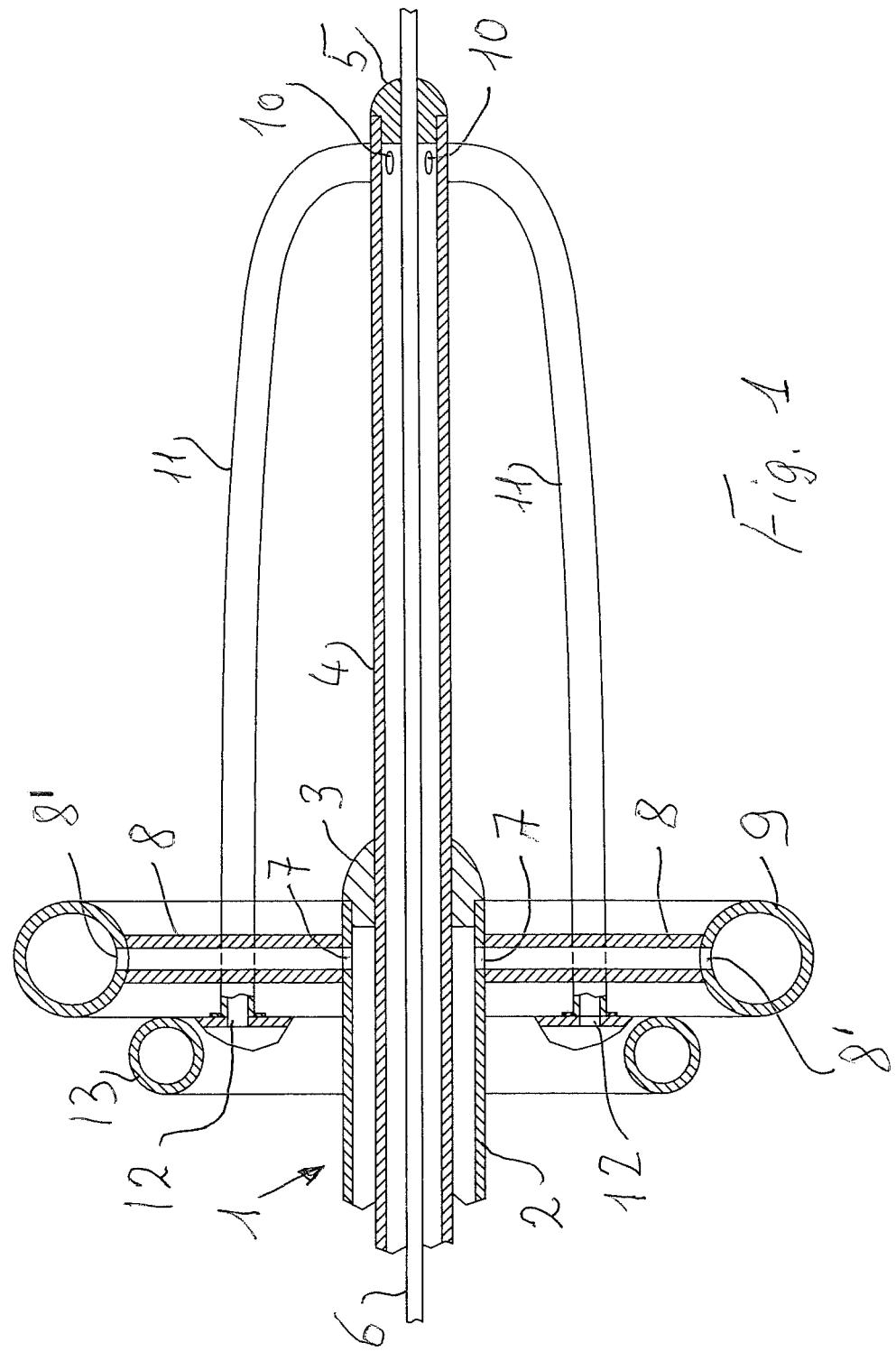
FIG. 1 is a longitudinally sectioned side view, on a larger scale, of the distal end of a catheter according to the invention with the tubular elements partially inflated.
Figure 2:
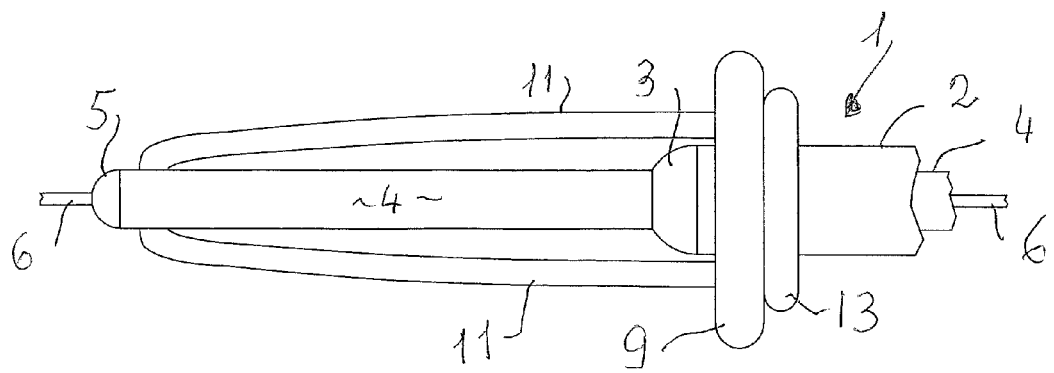
FIG. 2 is a side view of the distal end of the catheter according to FIG. 1, with the tubular elements almost completely deflated.
Figure 3:
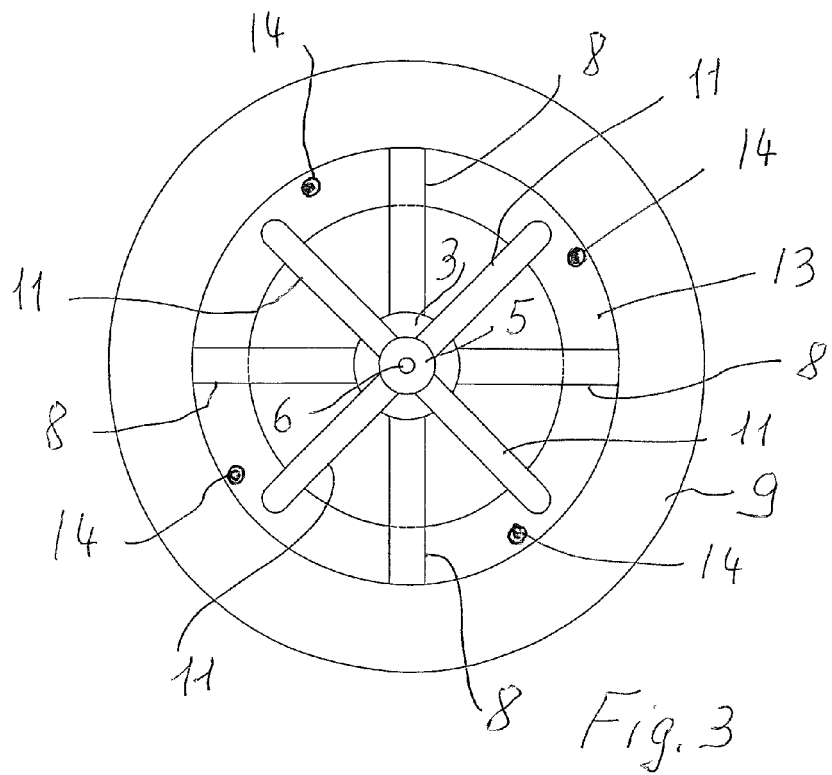
FIG. 3 is a front view of the distal end of the catheter according to FIGS. 1 and 2, with the tubular elements inflated.

With reference now to the drawings and with reference to FIGS. 1 to 3 thereof, 1 denotes a catheter according to the invention. This catheter 1 comprises a first tubular element 2 which extends from the proximal end (not shown) to the distal end thereof, which is closed by a closing element 3. A second tubular element 4 is housed coaxially with said tubular element 2 and extends from the proximal end (not shown) to the distal end thereof, passing through the closing element 3, so as to terminate at a short distance from the latter with a second closing element 5. The catheter is completed by a third, relatively rigid, rod-like, central element 6 which extends from the proximal end of the catheter, passing concentrically through the tubular element 4 externally through the closing element 5.

The tubular element 2 has, upstream of the closing element 3 and in the vicinity thereof, four radial holes 7 arranged in the same plane and staggered at 90° relative to each other, communicating via a corresponding number of tubular radial elements 8 and the holes 8' with a toroidal tubular element 9 which is coaxial with the tubular element 2, for the purposes which will be explained below.

The tubular element 4 has, upstream of the closing element 5 in the vicinity thereof, four holes 10 communicating with four tubular elements 11 which extend behind beyond the plane defined by the toroidal element 9 so as to be connected via the holes 12 in fluid communication with a toroidal element 13 which has a diameter smaller than the diameter of the toroidal element 9. The holes 10, and therefore the tubular elements 11, are staggered by 45° with respect to the holes 7, and therefore with respect to the tubular elements 8, as is shown more clearly in FIG. 3. The toroidal element 13 also has a series of radio-opaque markers 14 for the purposes which will be described below.

Figure 4:
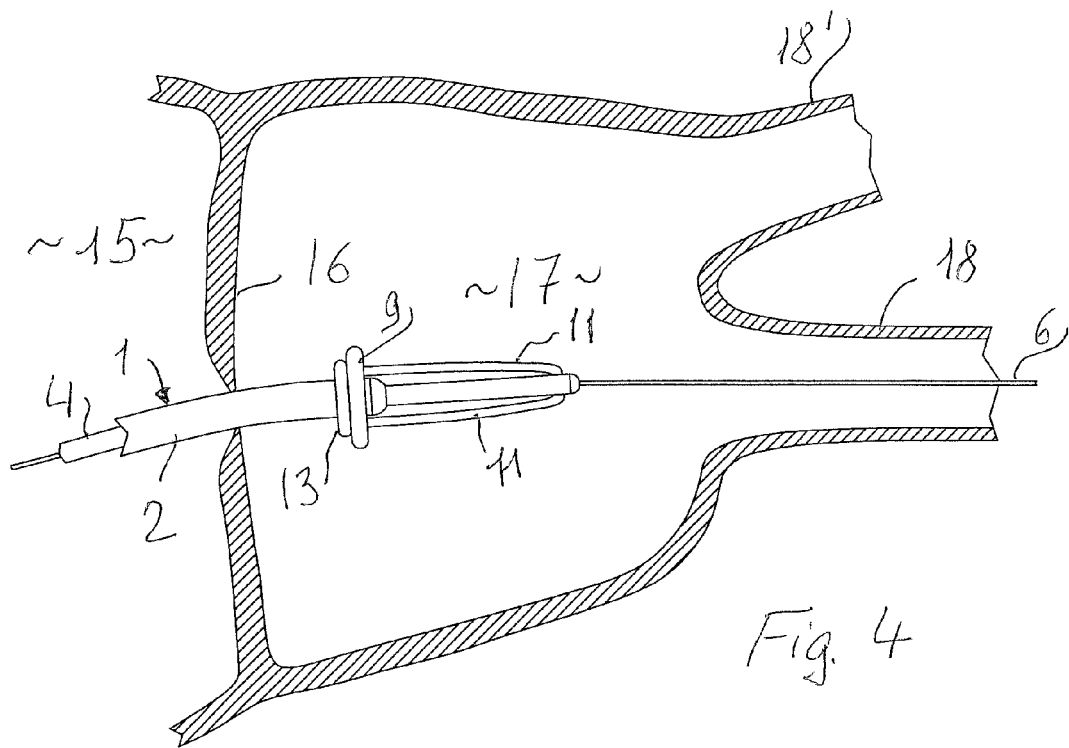
FIG. 4 shows the passage of the catheter according to the invention from the right atrium of the heart into the left atrium through the interatrial septum.
Figure 5:
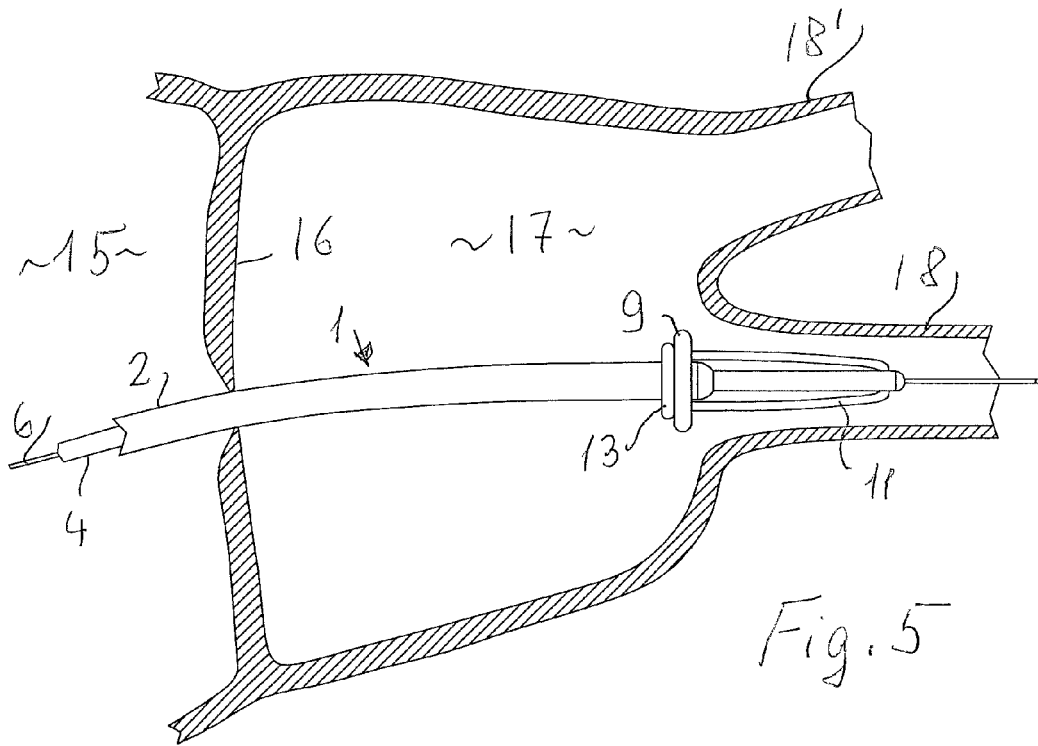
FIG. 5 shows the introduction of the catheter according to the invention into one of the pulmonary veins emerging inside said atrium.

During operation, the device described is completely deflated, as shown in FIG. 2, and retracted along the tubular elements 4 and 2 of the catheter 1. At this point the catheter thus prepared is introduced, by passing it down from the upper vein into the foramen ovale in the right atrium 15 of the patient's heart (see FIGS. 4 and 5) and from here, after perforation of the interatrial septum 16, into the left atrium 17 of the patient's heart where the pulmonary veins emerge, entering in sequence (FIG. 5) each pulmonary vein 18, 18' for the ablation treatment.

Figure 6:
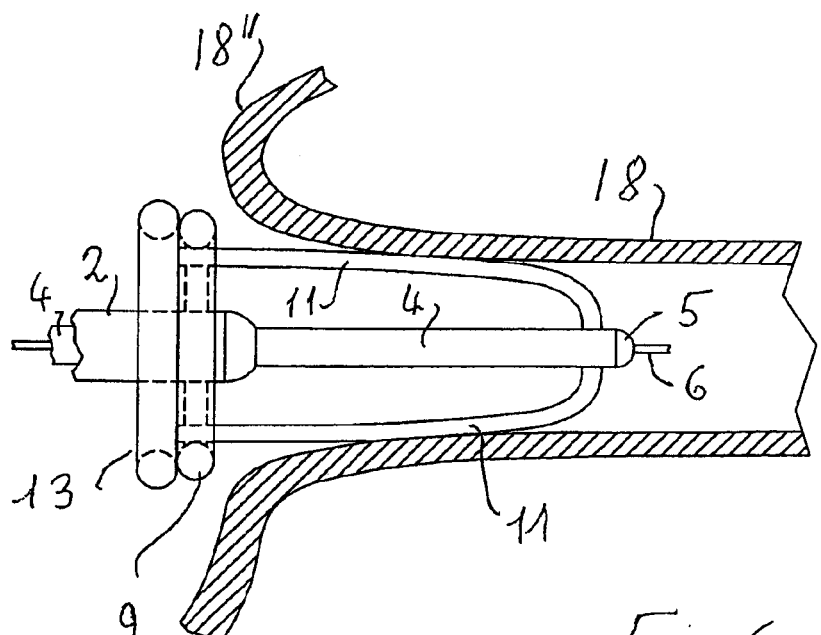
FIG. 6 shows the positioning of the inflatable cage of the catheter inside the mouth of said pulmonary vein.

Owing to the presence of the radio-opaque markers 14, the optimum positioning of the device is greatly facilitated. At this point, fluid is injected through the tubular element 4 of the catheter. This fluid then flows from the proximal end of the tube 4 to its distal end and from here through the holes 10 into the arms 11 and from the latter through the holes 12 into the toroidal element 13 which are thus inflated. Owing to the independent movement of the arms 11 of the system positioning cage, the latter perfectly adapts to the anatomy of the pulmonary vein concerned, allowing the resilient inflatable chamber to adapt to the dimensions and form of the orifice (FIG. 6).

Figure 7:
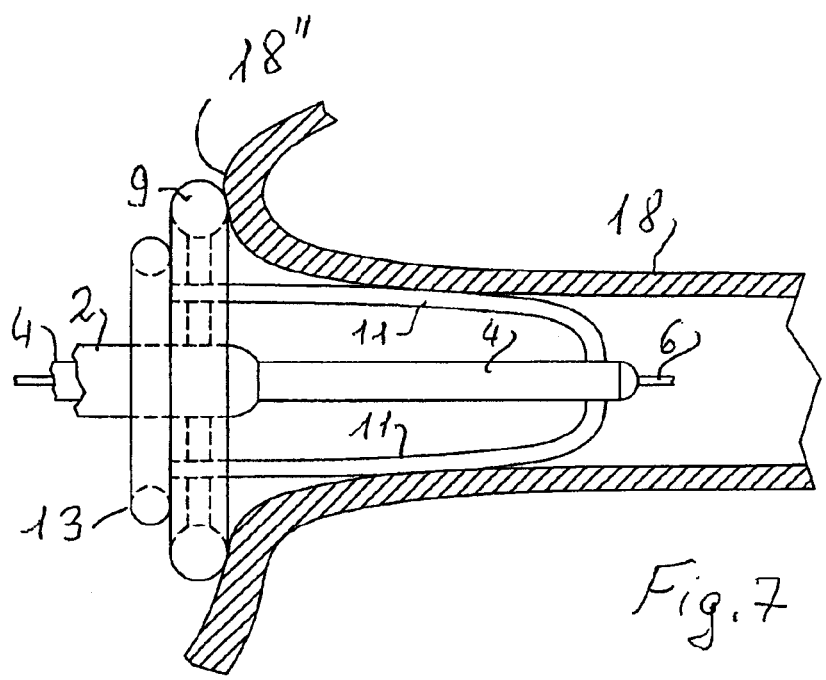
FIG. 7 shows the inflation of the annular element for cryoablation of the orifice of said vein.

At this point the cryogenic fluid is introduced, via the tubular element 1, holes 7, radial tubes 8 and holes 8', into the cryothermal chamber 9 which is thus inflated (FIG. 7) so as to cause it to rest circumferentially on the orifice 18" of the pulmonary vein 18, thus performing cryoablation of the tissue at the orifice of said vein.

At this point, both the cryothermal chamber 9 and the positioning cage 11, 13 are deflated again, and the catheter may again be extracted, passing it along the same path in the reverse direction.

The advantages of the present device will be clear: owing to the cage formed by the arms 11 and the toroidal element 13 which can be inserted into the mouth of the pulmonary vein, the device can be stably and precisely positioned in relation to the tissue to be ablated, also owing to the presence of the radio-opaque markers 14. Moreover, this cage may also be inflated with a radio-opaque liquid so as to facilitate even more precise positioning thereof with respect to the tissue to be ablated.

In particular, although in the description above the use of a cryogenic fluid as ablation element has been described purely by way of an example, it is understood that this ablation element may be an electrically powered ablation element; a thermal ablation element; an ultrasound ablation element; a microwave ablation element; a fluid-type ablation element; a light-emitting ablation element or generally an ablation element which uses any form of energy available.

Therefore the present invention is not limited to the embodiment shown and described, but comprises all those variations and modifications which fall within the wider scope of the inventive idea, substantially as claimed below.

The invention claimed is:

1. A device for electrically isolating the pulmonary veins in atrial fibrillation for treatment thereof by means of ablation of a circumferential zone of tissue in a position where a pulmonary vein extends from an atrium, comprising:
a catheter having a terminal part and a distal part and comprising a first tubular element; a second tubular element concentric with said first tubular element and an axial rod-like element which extends beyond the distal end of said first and second tubular elements; a first tubular toroidal element supported by a plurality of tubular arms which extend from said distal end towards said toroidal element forming a kind of cage which can be opened in umbrella fashion around the distal end of said catheter said tubular arms and said toroidal element being in fluid communication with each other and with said second tubular element of said catheter;
and a second toroidal tubular element in fluid communication by means of the radial arms with said first tubular element of said catheter, all of which so that in a first operating condition said first and second toroidal elements with the associated tubular arms are deflated and made to adhere to said distal end of the catheter; in a second operating condition said distal end of the catheter is inserted inside an orifice of a pulmonary vein and a fluid is pumped into said first toroidal element and into said arms so as to position said arms against the orifice of the pulmonary vein; and in a third operating condition an ablation element is introduced and/or activated inside said second toroidal element, inflating it and bringing it into contact with the orifice of the said pulmonary vein for ablation of a circular zone of tissue around the orifice of the said vein.

2. The device according to claim 1, wherein said ablation element comprises a cryoablation element.

3. The device according to claim 1, wherein said ablation element comprises an electrically powered ablation element.

4. The device according to claim 1, wherein said ablation element comprises a thermal ablation element.

5. The device according to claim 1, wherein said ablation element comprises an ultrasound ablation element.

6. The device according to claim 1, wherein said ablation element comprises a microwave ablation element.

7. The device according to claim 1, wherein said ablation element comprises a fluid-type ablation element.

8. The device according to claim 1, wherein said ablation element comprises a light-emitting ablation element.

9. The device according to claim 1, wherein said arms are provided with radio-opaque markers.

10. The device according to claim 1, wherein a radio-opaque fluid is pumped into said arms.

11. The device according to claim 1, wherein said first and said second toroidal elements and said arms are made of resilient material.

* * * * *